US007225360B2

(12) United States Patent
Kihara (10) Patent No.: US 7,225,360 B2
(45) Date of Patent: May 29, 2007

(54) AUTOMATIC ANALYSIS APPARATUS AND METHOD FOR CONTROLLING AN ANALYSIS UNIT

(75) Inventor: Takayuki Kihara, Kyoto (JP)

(73) Assignee: Shimadzu Corporation, Kyoto-shi (JP)

( * ) Notice: Subject to any disclaimer, the term of this patent is extended or adjusted under 35 U.S.C. 154(b) by 510 days.

(21) Appl. No.: 10/803,401

(22) Filed: Mar. 18, 2004

(65) Prior Publication Data

US 2004/0216009 A1 Oct. 28, 2004

(30) Foreign Application Priority Data

Mar. 24, 2003 (JP) ............................. 2003-080816

(51) Int. Cl.
*G06F 11/00* (2006.01)
(52) U.S. Cl. ..................... 714/37; 714/25; 714/26; 714/30; 714/38; 709/224; 73/61.52
(58) Field of Classification Search ................ 709/224; 714/25, 26, 30, 37, 38; 73/61.52
See application file for complete search history.

(56) References Cited

U.S. PATENT DOCUMENTS

| 6,065,136 | A | 5/2000 | Kuwabara |
| 6,473,812 | B2 * | 10/2002 | Motoyama .................. 710/15 |
| 2003/0055952 | A1 * | 3/2003 | Motoyama et al. ......... 709/224 |

FOREIGN PATENT DOCUMENTS

| JP | 10-215494 | 8/1998 |
| JP | 10-228311 | 8/1998 |
| JP | 10-308737 | 11/1998 |
| JP | 2002-372543 | 12/2002 |

OTHER PUBLICATIONS

"Wireless LAN" Microsoft Computer Dictionary. Fifth Edition. Copyright 2002. Microsoft Press.*

* cited by examiner

*Primary Examiner*—Robert Beausoliel
*Assistant Examiner*—Joseph D Manoskey
(74) *Attorney, Agent, or Firm*—Rankin, Hill, Porter & Clark LLP (57) ABSTRACT

When an instruction by a person in charge is required during an analysis operation, a transmitted e-mail processing unit creates an e-mail that includes, as a message or an attached file, information concerning data to be currently analyzed and an analysis condition, and transmits the e-mail to the e-mail address of the person in charge. The person in charge, at a remote area, employs a locally available PC to read the e-mail, and transmits, to an analysis apparatus, a response e-mail that includes an instruction command. The e-mail is read through a communication controller, and a received case name confirmation unit and a sender verification unit examine the received e-mail to determine whether it is a control e-mail issued by an authorized sender. Thereafter, a command extraction unit extracts a control command from the e-mail. Upon receiving this command, an analysis controller controls the individual sections of an analysis unit.

8 Claims, 6 Drawing Sheets

```
TRANSMISSION SERVER          : LC#1
TRANSMISSION DATE AND TIME   : 19:58, AUGUST 2, 2002
DESTINATION                  : ○○○○
CASE NAME                    : REPORT OF STATUS OF AUTOMATIC ANALYSIS LC#1

SINCE RESULTS OF THE FOLLOWING REPRODUCTION TEST SHARED A DISQUALIFICATION,
THE ANALYSIS OPERATION WAS HALTED.

DATE AND TIME   2002/8/2 19:55
CATEGORY    RETENTION TIME
THE NUMBER OF DATA SETS USED      7
THE NUMBER OF IDENTICAL PEAKS     5

INDIVIDUAL PEAK CV VALUES  1.3%   0.8%   8.1%(DISQUALIFIED)  1.7%   2.2%
PEAK 1 DATA                1.11   1.13   1.14   1.15   1.15   1.15   1.15
PEAK 2 DATA                1.72   1.71   1.71   1.75   1.72   1.71   1.71
PEAK 3 DATA                2.30   2.50   2.90   2.50   2.50   2.40   2.30
PEAK 4 DATA                3.10   3.00   3.00   3.00   3.10   3.10   3.10
PEAK 5 DATA                4.50   4.50   4.55   4.57   4.55   4.57   4.80

DO YOU WANT TO RESUME THE ANALYSIS OPERATION?
A : RESUME ANALYSIS
B : PERFORM ANALYSIS AGAIN FROM THE BEGINNING, AFTER AN ANALYSIS CONDITION IS STABILIZED.
    →PLEASE DESIGNATE AN ANALYSIS CONDITION SETUP FILE.

1  : RINSE A COLUMN (ORGANIC SOLVENT)
2  : RINSE A COLUMN (ACID SOLVENT)
3  : REMOVE BUBBLES
4  : PREPROCESS A
5  : PREPROCESS B
99 : ATTACH A METHOD FILE (PLEASE ATTACH A FILE)
C  : TRANSMIT AN ANALYSIS CONDITION
```

FIG. 6

|   | A | B | C | D | E | F |
|---|---|---|---|---|---|---|
| 2 |   |   |   |   |   |   |
| 3 |   | METHOD FILE NAME | METHOD1 |   |   |   |
| 4 |   |   |   |   |   |   |
| 5 |   | ANALYSIS CONDITION |   |   |   |   |
| 6 |   |   |   |   |   |   |
| 7 |   | FLOW RATE OF LIQUID | A | 0.2 | μL/min |   |
| 8 |   |   | B | 0.2 | μL/min |   |
| 9 |   |   | C | 0 | μL/min |   |
| 10 |   | UPPER PRESSURE LIMIT VALUE | A | 10 | MPa |   |
| 11 |   |   | B | 0 | MPa |   |
| 12 |   |   | C | 0 | MPa |   |
| 13 |   |   |   |   |   |   |
| 14 |   | COLUMN TEMPERATURE |   | 40 | °C |   |
| 15 |   |   | UPPER LIMIT VALUE | 65 | °C |   |
| 16 |   |   |   |   |   |   |
| 17 |   | DETECTOR A | ANALYSIS PERIOD | 5 | min |   |
| 18 |   |   | WAVELENGTH | 245 | nm |   |
| 19 |   |   | SAMPLING RATE | 100 | msec |   |
| 20 |   |   |   |   |   |   |
| 21 |   | DETECTOR B | ANALYSIS PERIOD | 5 | min |   |
| 22 |   |   | WAVELENGTH | 245 | nm |   |
| 23 |   |   | SAMPLING RATE | 100 | msec |   |
| 24 |   |   |   |   |   |   |
| 25 |   | PEAK DETECTION | WIDTH | 1 | sec |   |
| 26 |   |   | SLOPE | 10000 | μV/sec |   |
| 27 |   |   | DRIFT | 1000 | μV/hour |   |

\METHOD\DETERMINATION METHOD/

AUTOMATIC ANALYSIS APPARATUS AND METHOD FOR CONTROLLING AN ANALYSIS UNIT

BACKGROUND OF THE INVENTION

1. Field of the Invention

The present invention relates to an automatic analysis apparatus for performing a continuous operation for an extended period of time, and a method for controlling an analysis unit for analyzing an object to be analyzed. More particularly, the present invention relates to a technique for remotely controlling or monitoring the automatic analysis apparatus.

2. Description of the Related Art

For an analysis using a liquid chromatograph, for example, there is a case wherein measurements are conducted continuously for an extended period of time, or wherein a great number of samples are exchanged automatically. For an analysis apparatus that performs an automatic operation for an extended period of time, the operation is frequently, substantially performed unattended, and the person in charge is not standing by near the analysis apparatus. When an abnormality occurs during the analysis operation, or a decision by a person is required to continue the operation, the person in charge must take some action, such as interrupting or halting the apparatus or changing a parameter, whatever is appropriate under the circumstances.

To cope with this situation, in a related-art system, as described in Japanese publications JP-A-10-215494 and JP-A-10-228311, when an abnormality or a defect occurs during an analysis, the analysis can not be continued and an e-mail describing the problem is automatically created and transmitted to a previously registered destination. According to this system, a person in charge who is located at a distance from the analysis apparatus can use a locally available personal computer to read the e-mail and identify the abnormality at the analysis apparatus, and can perform an appropriate process.

In the related-art, when the person in charge located a remote location is notified of an abnormality at an analysis apparatus or of the need to enter a specific setup for the analysis apparatus, a client/server technique has been employed to perform a remote operation or to remotely control the analysis apparatus. Specifically, a personal computer (hereinafter referred to as a "PC") that controls the analysis apparatus is connected, as a server, to a network such as the Internet or the Intranet. A PC that serves as a client terminal, and is locally available to the person in charge, is connected to the same network and transmits a predetermined command to the server. As a result, the analysis apparatus can be controlled by the client terminal in the same manner as it is by the server.

However, in order to enable the remote control, the client/server system must be constructed, and the remote operation can be performed only by a client terminal (or a server) for which specific software has been provided in advance. Therefore, when the locally available PC is not such a client terminal, the person in charge must move to a location where an appropriate client terminal is installed to perform the remote operation. Thus, when the analysis operation is interrupted or halted due to the occurrence of an abnormality, the resumption of the operation can not always be performed rapidly, and either the analysis operation will be delayed, or an important change or indication of an object to be analyzed will be overlooked.

SUMMARY OF THE INVENTION

To resolve these problems, it is an object of the present invention to provide an automatic analysis apparatus that can, upon the occurrence of an abnormality or upon the need to enter a data setup, quickly perform an appropriate process to continue or resume an analysis operation, even when the person in charge is located at a distance from the analysis apparatus, and a method for controlling an analysis unit for analyzing an object to be analyzed.

To achieve the object, an automatic analysis apparatus according to the present invention comprises:

a) an analysis unit for analyzing an object to be analyzed;

b) a reception unit for receiving a control e-mail via a wire line or a wireless communication line;

c) a data extraction unit for extracting a specific data from the control e-mail; and d) a control unit for controlling the analysis unit based on the specific data extracted by the data extraction unit. In the automatic analysis apparatus, the data extraction unit may extract the specific data from a message in the control e-mail, or a data contained in an attached file of the control e-mail.

To control, from a remote area, an automatic analysis apparatus according to the present invention, a person in charge of an analysis employs a locally available tool, such as a PC, a portable telephone or a portable information terminal that can generate and transmit an e-mail, to generate either a control e-mail, a message of which includes specific data consonant with the contents of a desired operation, or a control e-mail, to which a data file including the specified data is attached, and transmits the control e-mail to a previously designated destination. According to the automatic analysis apparatus of the invention, a reception unit reads, via a communication line, e-mails accumulated by a predetermined mail server that are addressed to the pertinent apparatus. When the control e-mail is included in the e-mails, a data extraction unit extracts the specified data from the message included in the control e-mail or from the data included in the attached file. Based on the content of the specified data, a control unit controls an analysis unit by activating or halting a specific section of the analysis unit, or by changing a parameter.

When the Internet is employed as the communication line, a PC in which special software has been installed is not particularly required, and so long as a common tool that can transmit an e-mail is locally available, the person in charge can control the analysis unit at any location whereat a connection to the Internet environment is available. Therefore, when the analysis apparatus must be operated or controlled from a remote area, an appropriate operation or control can be quickly performed, and a loss due to the interruption or the halting of an analysis can be reduced. Furthermore, since a related-art e-mail system is employed, the installation costs for the addition of a special software function can be eliminated.

While the remote control of the analysis apparatus by the person in charge of an analysis may be performed based on the voluntary intent of the person, in many cases, the remote control may be performed due to the occurrence of an abnormality at the analysis apparatus or because there is a need for a specific human decision. Therefore, preferably, the automatic analysis apparatus of the present invention further comprises:

e) a mail creation unit for creating a notification e-mail based on various data generated during an analysis process; and f) a transmission unit for transmitting the notification e-mail created by the mail creation unit through the communication line to a predetermined destination. The reception unit receives a response e-mail, as the control e-mail, through the communication line in response to the notification e-mail that was previously transmitted from the transmission unit. In the automatic analysis apparatus, the mail creation unit may create the notification e-mail which includes a message written based on various data generated during the analysis process, or to which a data file prepared based on various data generated during the analysis process is attached.

With this configuration, when a specific problem has been encountered during an analysis operation performed by the analysis apparatus, or when a specific decision by the person in charge of the analysis is required to continue or halt the analysis, the mail creation unit creates a notification e-mail having a predetermined form, which includes a message written based on various data that should be reported to the person in charge, or to which a data file prepared based on various data is attached. The transmission unit transmits the prepared notification e-mail to a predesignated e-mail address for the person in charge, and the notification e-mail is accumulated by a predetermined mail server. The person in charge employs a locally available PC, a portable telephone or a portable information terminal to read e-mails, one after another or periodically, obtained from the mail server, and confirms the contents of the e-mails. When the notification e-mail is included in the e-mails, the person in charge transmits a response e-mail as the control e-mail in response to the information described in the notification e-mail.

With this arrangement, regardless of where the person in charge is, he or she can precisely ascertain the state of the analysis apparatus, e.g. the cause of a defect, by reading the notification e-mail, and can quickly transmit the control e-mail to instruct an appropriate operation or control instruction. Therefore, when a problem has occurred at an automatic analysis apparatus that requires an instruction by the person in charge, a necessary process can be performed by quickly receiving an instruction from the person in charge, and the length of the time, during which the analysis operation is interrupted or halted, can be reduced.

DETAILED DESCRIPTION OF THE INVENTION

An automatic analysis apparatus according to a first embodiment of the present invention will now be described while referring to FIGS. 1 and 2. A liquid chromatograph is employed for the analysis apparatus; however, another analysis apparatus can also be employed.

Figure 1:
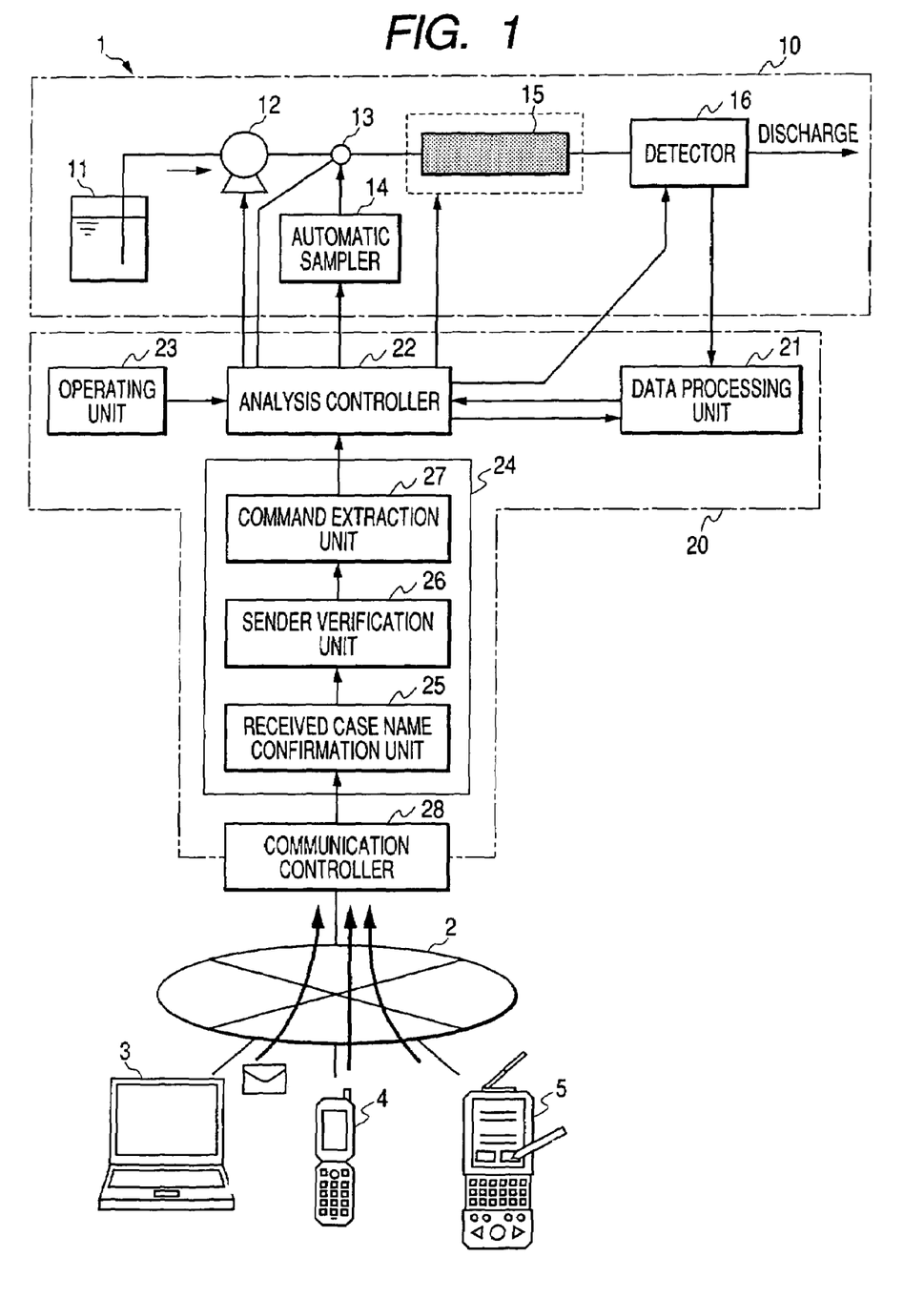
FIG. 1 is a diagram showing the general configuration of a remote analysis system including an automatic analysis apparatus according to a first embodiment of the present invention.
Figure 2:
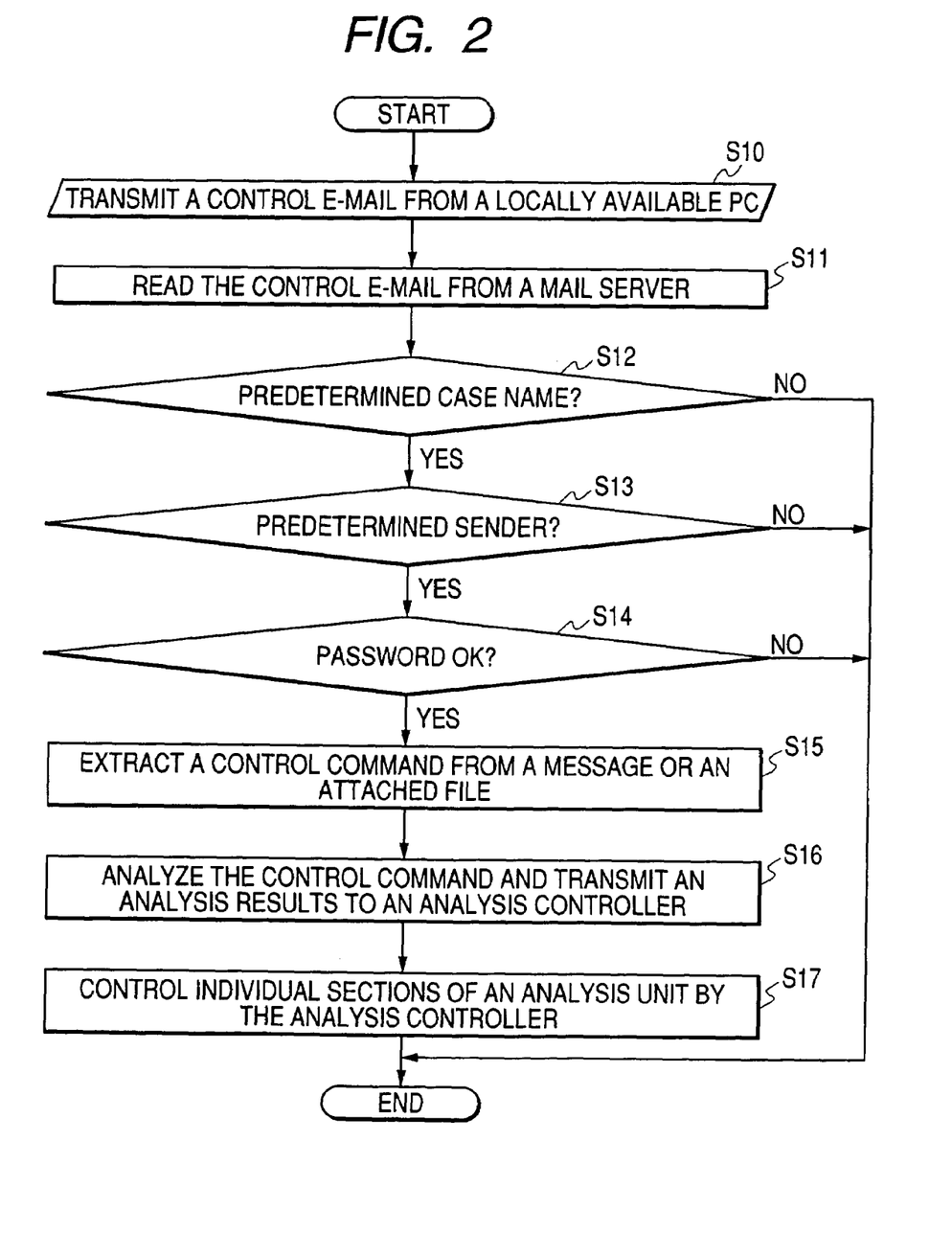
FIG. 2 is a flowchart showing the operation of the automatic analysis apparatus in FIG. 1.

FIG. 1 is a diagram showing the general configuration of a remote analysis system that includes the automatic analysis apparatus for this embodiment. In the remote analysis system, an automatic analysis apparatus 1 installed at an analysis site is connected, through the Internet 2, to a PC 3, a portable telephone 4 or a portable information terminal 5 that is locally available to a person in charge who is located at a distance from the analysis site. Standard e-mail software is installed on the PC 3, the portable telephone 4 or the portable information terminal 5 (e.g., Outlook Express (a trademark of Microsoft Corp.), available from Microsoft Corp., is installed on the PC 3), and normal e-mail transmission and reception is enabled by using a mail server provided by a contracted provider.

The automatic analysis apparatus 1 comprises an analysis unit 10 and a PC 20. The analysis unit 10 conducts the measurement of samples and obtains the data required for an analysis. The PC 20 includes a data processing unit 21, an analysis controller 22, a received e-mail processing unit 24, a communication controller 28, and an operating unit 23. The data processing unit 21 performs a predetermined waveform process and a predetermined arithmetic operation for the obtained data, and prepares the analysis results. The analysis controller 22 controls the individual operations of the analysis unit 10. The received e-mail processing unit 24 transmits a control signal to the analysis controller 22 in accordance with an e-mail (control e-mail), which will be described later, that is received from the outside. The communication controller 28 connects to the Internet 2. The operating unit 23 is a pointing device such as a keyboard or a mouse.

The analysis unit 10 includes an eluant tank 11, a liquid feed pump 12, an auto-injector 13, an automatic sampler 14, a column 15 and a detector 16. The analysis controller 22 totally controls the operations of the individual sections of the analysis unit 10. The received e-mail processing unit 24, which is one of the features of the automatic analysis apparatus 1 for this embodiment, includes a received case name confirmation unit 25, a sender verification unit 26 and a command extraction unit 27. The received e-mail processing unit 24 transmits an extracted command to the analysis controller 22.

In the automatic analysis apparatus, in accordance with various analysis conditions, data processing conditions and various other instructions that are entered through the operating unit 23, the analysis controller 22 controls the operations of the individual sections of the analysis unit 10 and performs an LC analysis for a target sample. That is, when the analysis is started in the analysis unit 10, an eluate (mobile phase) is transmitted, under suction produced by the liquid feed pump 12, to the column 15 from the eluant tank 11 at a substantially constant flow rate. Samples are selected in a predetermined order by the automatic sampler 14 and are injected into the eluate by the auto injector 13, and the resultant samples are supplied to the column 15. The samples being passed through the column 15 are separated into sample components, and then these components are sequentially detected by the detector 16, and detection signals are transmitted to the data processing unit 21 from the detector 16. In accordance with a predetermined analysis algorithm, the data processing unit 21 performs the data processing for the received data and generates a chromatogram, or performs a qualitative analysis or a quantitative analysis based on the chromatogram.

The analysis operation based on the setup or on an instruction entered by the operating unit 23 is the same as the one performed by a related-art apparatus. In addition to this, in the automatic analysis apparatus 1 in this embodiment, the analysis controller 22 controls the operations of the individual sections of the analysis unit 10 in accordance with a command received from the received e-mail processing unit 24. This control operation will now be described, while referring to the flowchart in FIG. 2, by employing an activation processing wherein the automatic analysis apparatus 1 in the OFF state is powered ON to immediately start the analysis as an example.

When the automatic analysis apparatus 1 in the OFF state is to be activated, a system check or a calibration process is performed. Further, since the stable state of the detector 16 cannot be immediately obtained depending on the type of the detector 16, a specific period of time is required from the time the apparatus is powered on until the apparatus is actually ready to start the analysis. Therefore, when a person in charge make the analysis start immediately after a specific time, he or she needs to issue an instruction for activating the automatic analysis apparatus 1 at the time before the specific time by a predetermined time period.

Specifically, the person in charge who is at a distance from the automatic analysis apparatus 1 employs the locally available PC to activate the e-mail software and creates a control e-mail. In this case, the form of the control e-mail is determined in advance, for example, the control e-mail includes a message column, a case name column and an address column. An apparatus control command is written to the message column using a predetermined code. Further, predetermined text is written to the case name column, and a predetermined e-mail address is designated in the address column as a transmission destination. Further, a previously determined password is entered in the message or in the header to verify the sender, which will be described later. The person in charge creates this special e-mail (control e-mail), and performs a predetermined transmission operation (step S10). Then, the control e-mail is transmitted through the Internet 2 and is held by the mail server (included in the Internet 2 in FIG. 1) of the automatic analysis apparatus 1.

The PC 20 of the automatic analysis apparatus 1 is constantly connected to the Internet 2, and reads e-mails from the mail server periodically, at a comparatively short time intervals. Or, when a new e-mail has arrived at the mail server, the mail server notifies the PC 20 of the arrival of the new e-mail, and upon receiving this notification, the PC 20 reads the e-mail (step S11). In either case, it is preferable that the e-mail that has arrived at the mail server be read with as little delay as possible. When the received e-mail processing unit 24 obtains the e-mail through the communication controller 28, the received case name confirmation unit 25 determines whether the text data entered in the case name column of the received e-mail conforms to a predetermined form, so that whether the e-mail is the control e-mail addressed to the automatic analysis apparatus 1 can be identified (step S12).

When it is confirmed that the received e-mail is a control e-mail, a verification process is performed to determine whether the sender of the e-mail is authorized to operate or control the automatic analysis apparatus 1. First, the sender verification unit 26 determines whether name of the sender conforms to a predetermined name (step S13), and then determines whether the password included in the received e-mail is the preregistered one (step S14). When the decisions at steps S12, S13 and S14 are YES, it is verified that the received e-mail has been issued by the authorized sender. Instead of this verification process, various other verification methods can be employed.

In accordance with predetermined procedures, the command extraction unit 27 extracts, from the thus verified e-mail, a control command that is included in the message included in the e-mail or in an attached file of the e-mail (step S15) In the first embodiment, the apparatus control command written using a predetermined code can be extracted from the message column. The command extraction unit 27 analyzes the extracted control command, converts the command into a form readable by the analysis controller 22, and transmits the converted command to the analysis controller 22 (step S16). In the same manner as is performed when an operating signal is received from the operating unit 23, the analysis controller 22 performs the control process in accordance with the converted command, i.e., make powering on the analysis unit 10 power on and performs a predetermined activation process (step S17).

As is described above, the person in charge, who is at a distance from the automatic analysis apparatus 1, need only employ the PC, the portable telephone 4 or portable information terminal 5 to transmit a control e-mail that includes a predetermined control command, so that the person in charge can permit the automatic analysis apparatus 1 to perform the activation process or various other operations. Since the received e-mail processing unit 24 confirms the case name of the received e-mail and verifies the sender, when an e-mail other than the control e-mail includes the same command by accident, or when a malicious third party transmits an e-mail that includes a control command, the inappropriate e-mail can be eliminated, and the performance of an erroneous operation can be prevented.

While referring to FIGS. 3 to 6, an explanation will now be given for a remote analysis system that includes an automatic analysis apparatus according to a second embodiment of the present invention. The automatic analysis apparatus 1 for the first embodiment controls the analysis operation simply in accordance with a command that is included in a control e-mail received from the outside. In the second embodiment, when a decision or an instruction issued by a person in charge is required, first, an automatic analysis apparatus 1 transmits an e-mail (notification e-mail) to the person in charge to report the current condition, and then the person in charge reads the e-mail and transmits to the automatic analysis apparatus 1 a response e-mail (control e-mail) that includes a necessary instruction and setup information.

Figure 3:
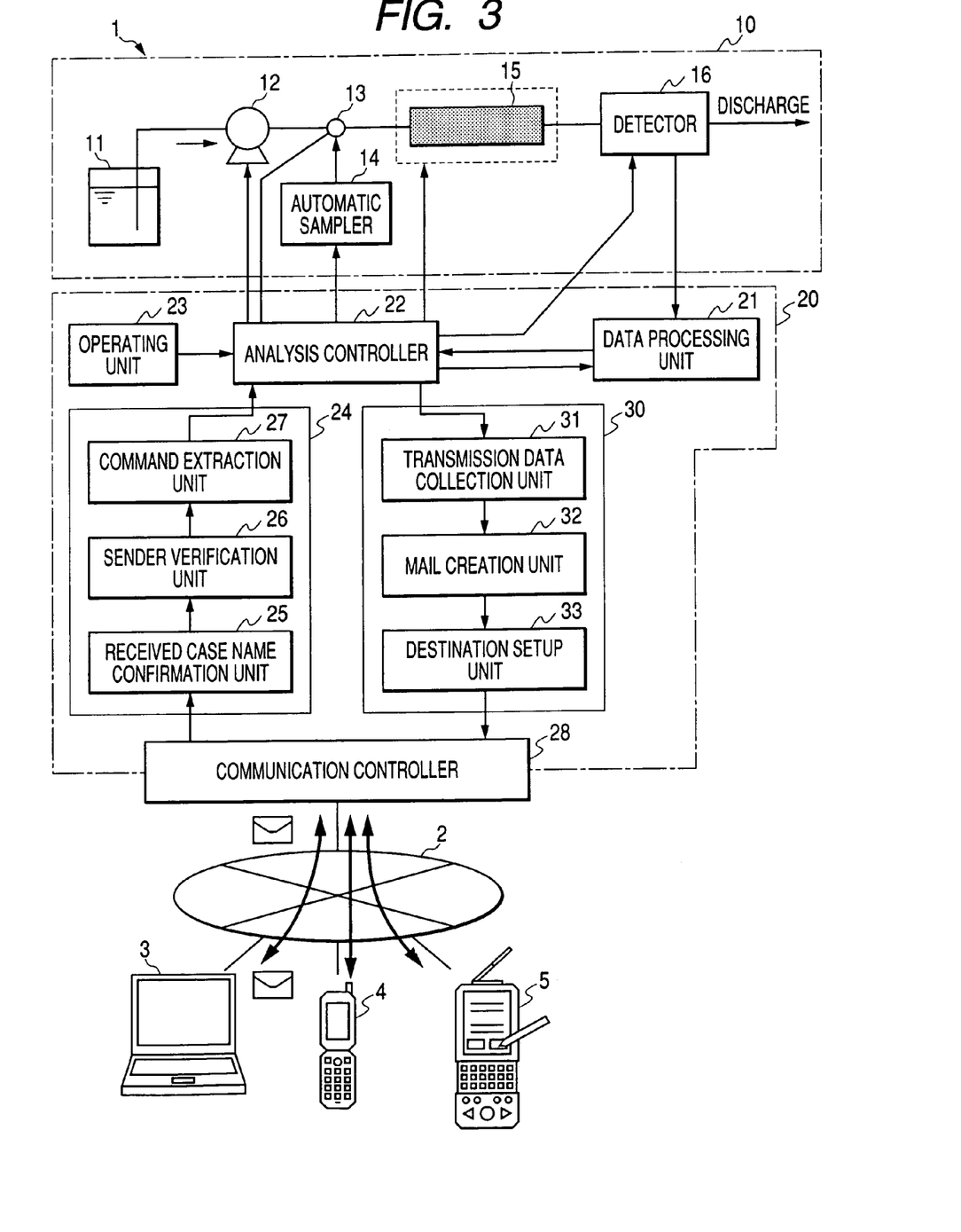
FIG. 3 is a diagram showing the general configuration of a remote analysis system including an automatic analysis apparatus according to a second embodiment of the present invention.

FIG. 3 is a diagram showing the configuration of the remote analysis system according to the second embodiment. The same reference numerals as used in FIG. 1 are also employed to denote corresponding components, and no further explanation for them will be given unless specifically required. As is apparent from FIG. 3, the automatic analysis apparatus 1 includes a PC 20 with a transmitted e-mail processing unit 30. The transmitted e-mail processing unit 30 includes a transmission data collection unit 31, an mail creation unit 32, and a destination setup unit 33. The transmission data collection unit 31 receives, from an analysis controller 22, various data to be transmitted to a person in charge. The mail creation unit 32 creates an e-mail that includes various data in a message or in an attached file. The destination setup unit 33 enters a preregistered e-mail address in an address column included in the e-mail.

Figure 4:
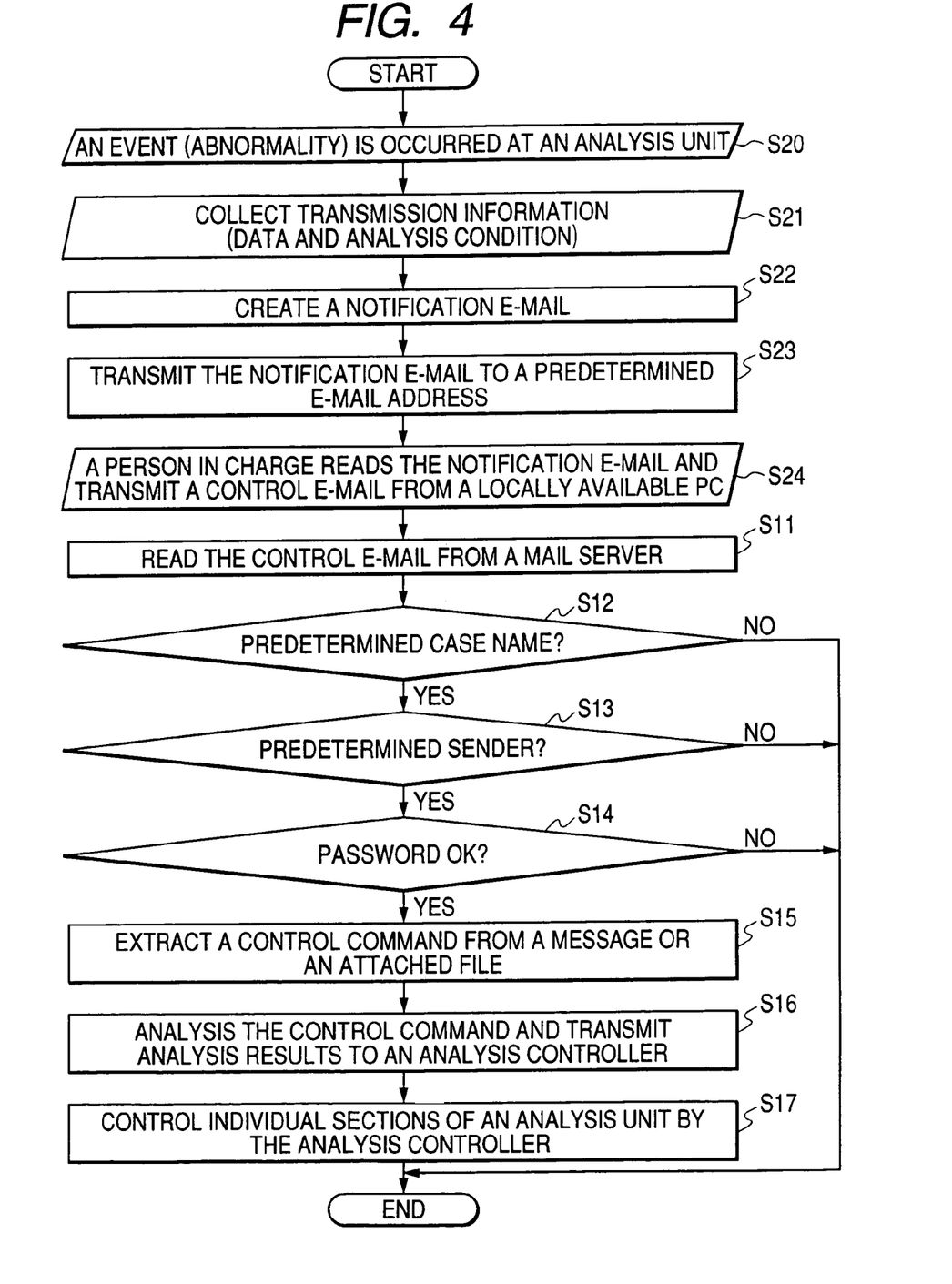
FIG. 4 is a flowchart showing the operation of the automatic analysis apparatus in FIG. 3.

While referring to the flowchart in FIG. 4, an explanation will now be given for the operation of the automatic analysis apparatus 1 performed when a defect has occurred in an analysis operation performed by an analysis unit 10. Assuming that the analysis unit 10, under the control of the analysis controller 22, is conducting a reproduction test through analysis of the same sample in order to manage the analysis quality, and that results obtained by the reproduction test show a disqualification because a reference value was not reached (step S20). The analysis controller 22 receives the results from a data processing unit 21, and controls the individual sections of the analysis unit 10 to temporarily halt the analysis operation.

Figure 5:
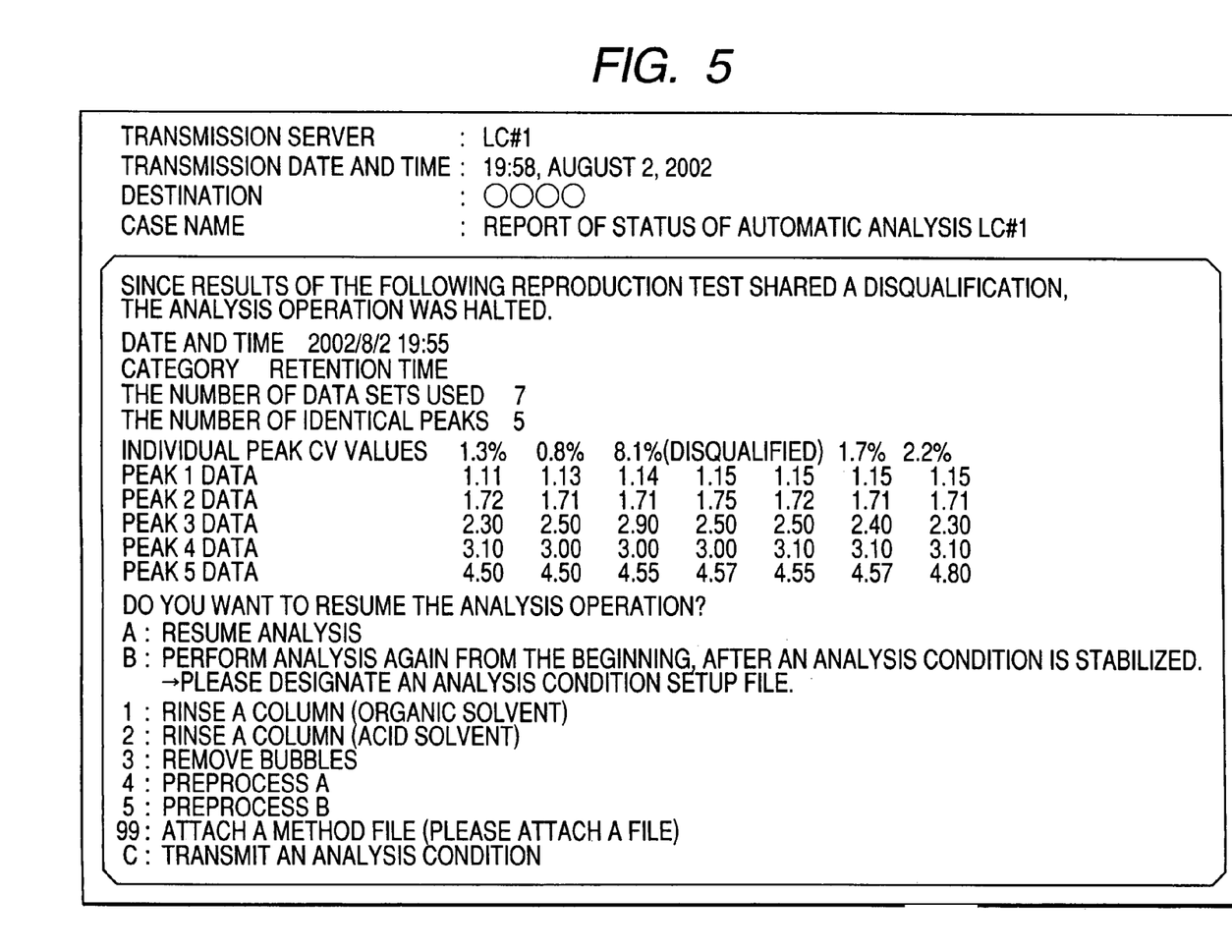
FIG. 5 is a diagram showing an example of a message included a notification e-mail created by the automatic analysis apparatus in FIG. 3.
Figure 6:
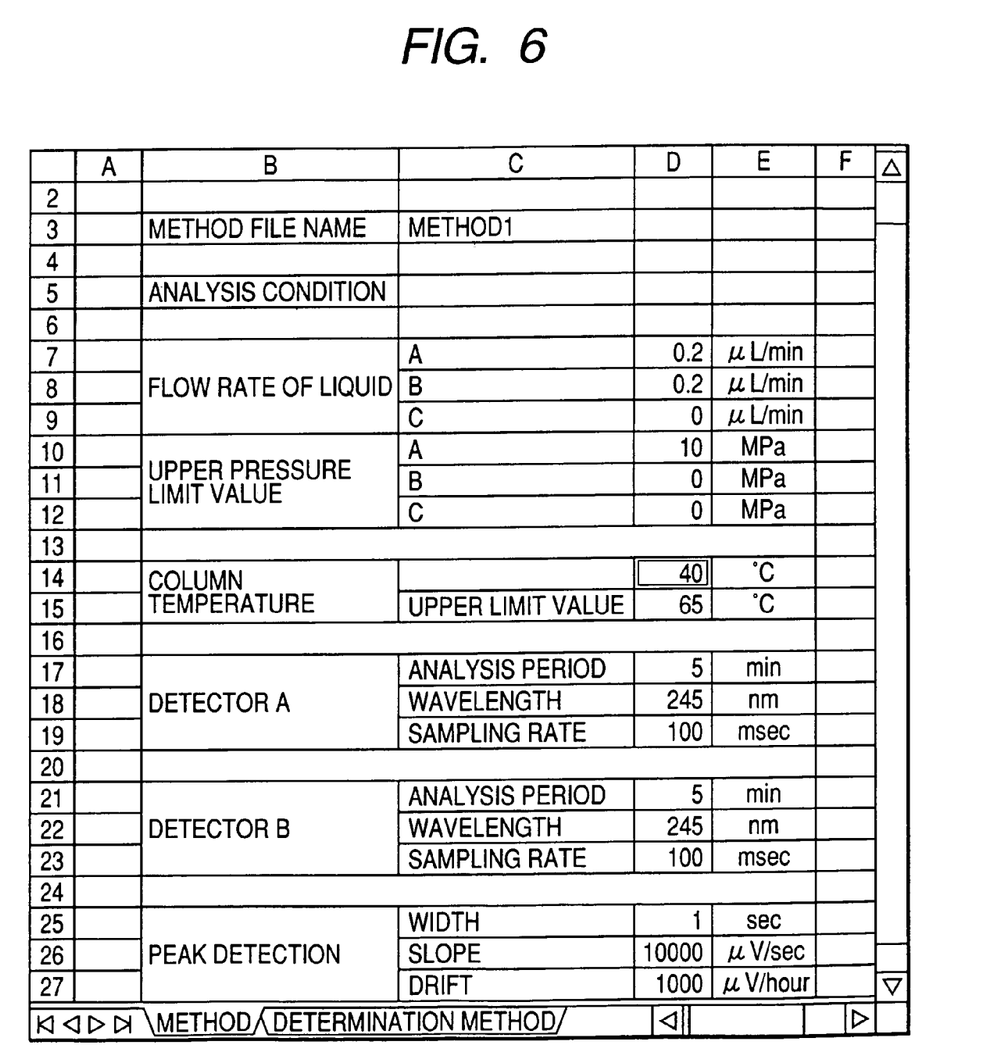
FIG. 6 is a diagram showing an example of a file attached to the notification e-mail created by the automatic analysis apparatus in FIG. 3.

The analysis controller 22 also instructs the transmission data collection unit 31 to create a notification e-mail. Upon receiving this instruction, the transmission data collection unit 31 collects, through the analysis controller 22, the data for the results of the reproduction test and the analysis condition used for the test (step S21). The mail creation unit 32 aggregates these data, and creates a message of the notification e-mail in accordance with a fixed format (step S22). An example of a message that is thus created for a notification e-mail is shown in FIG. 5, and an example of an attached file is shown in FIG. 6. In the second embodiment, data representing the analysis results are employed as a message, and the analysis condition is written in an Excel file of Microsoft Corp. (Excel is a trademark of Microsoft Corp.). Time data obtained by an internal timer is entered in an e-mail transmission date and time column, and predetermined character data is entered in a case name column and a sender column.

Instead of using the message column of the e-mail, a file form, such as a text form or a CSV form, that people can read and understand maybe employed to represent the analysis results data. In either case, when the e-mail has been created, the destination setup unit 33 inserts a predetermined e-mail address as a destination in an address column, and a communication controller 28 transmits this notification e-mail (step S23).

The notification e-mail is temporarily stored, through the Internet 2, in the e-mail box of a predetermined mail server. The person in charge employs locally available PC 3, a portable telephone 4 or a portable information terminal 5 to examine the arrival of an e-mail. When a new e-mail has arrived, the person in charge downloads the e-mail to the locally available tool, and confirms the contents of the message of the e-mail or the attached file of the e-mail (step S24). In the example message shown in FIG. 5, choices A, B, 1, 2, 3, 4, 5, 99 and C are prepared to resume the analysis operation.

Then, one choice is selected from choices in the message by using the response function of the e-mail software, and as needed, the contents of the changed file shown in FIG. 6 are changed and the altered file is attached to a return e-mail. A control e-mail (response e-mail) that is thus prepared by the person in charge is transmitted using the locally available tool, and is processed by a received e-mail processing unit 24 at the automatic analysis apparatus 1 through the procedures, described above, at steps S11 to S17. As a result, the analysis controller 22 performs control in accordance with a control command issued by the person in charge (in this case, one of the choices).

As is described above, in this embodiment, since the notification e-mail is transmitted from the automatic analysis apparatus 1 to the person in charge, the person in charge can know the state of the automatic analysis apparatus 1, and the status of the defect. Furthermore, when the notification e-mail includes choices for the person in charge to issue as an instruction, the person in charge need only select an appropriate choice and transmit the response e-mail including the selected contents. Therefore, the defect can be smoothly coped with, and especially when the locally available tool used by the person in charge is a device such as a portable telephone on which a satisfactory amount of data can not be displayed, the countermeasure can be easily taken.

Further, in order to permit the person in charge to know the state of the automatic analysis apparatus 1 more easily, various other data can be attached to the notification e-mail to be transmitted to the person in charge. For example, various statuses, such as those of a chromatogram, a pump pressure and a column temperature that are the designated analysis results, can be attached as graphs (still pictures) or moving pictures.

In the first and second embodiments, the liquid chromatograph apparatus has been employed as the analysis apparatus. However, various other analysis apparatuses can be employed. Further, these embodiments are merely examples, and can be appropriately modified or changed without departing from the scope of the invention.

What is claimed is:

1. An automatic analysis apparatus comprising:
   a) an analysis unit for analyzing an object to be analyzed;
   b) a mail creation unit for creating a notification e-mail based on a defect detected by the analysis unit;
   c) a reception unit for receiving a control e-mail from a person in charge via a wire line or a wireless communication line;
   d) a data extraction unit for extracting a specific data from the control e-mail; and
   e) a control unit for controlling the analysis unit based on the specific data extracted by the data extraction unit,
   f) wherein the notification e-mail is automatically sent to the person in charge,
   g) wherein the person in charge can cure the defect by selecting a choice from a plurality of choices contained in the notification e-mail and transmitting the choice as the specific data in the control e-mail to the analysis unit, and
   h) wherein the control unit resumes operation of the analysis unit upon curing the defect.

2. The automatic analysis apparatus according to claim 1, further comprising:
   i) a transmission unit for transmitting the notification e-mail created by the mail creation unit through the communication line to a predetermined destination,
   wherein the reception unit receives a response e-mail, as the control e-mail, through the communication line, in response to the notification e-mail that was previously transmitted from the transmission unit.

3. The automatic analysis apparatus according to claim 1, wherein the data extraction unit extracts the specific data from a message included in the control e-mail, or a data contained in an attached file of the control e-mail.

4. The automatic analysis apparatus according to claim 2, wherein the mail creation unit creates the notification e-mail, which includes a message written based on the various data generated during the analysis process, or an attached data file prepared based on the various data generated during the analysis process.

5. The automatic analysis apparatus of claim 1, wherein the control unit stops the operation of the analysis unit upon the detection of the defect.

6. The automatic analysis apparatus of claim 1, wherein the analyzing unit comprises a liquid chromatograph.

7. A method for controlling an analysis unit for analyzing an object to be analyzed, the method comprising:
- detecting a defect in the object;
- stopping operation of the analysis unit;
- creating a notification e-mail based on the defect;
- transmitting the notification e-mail to a person in charge of the analysis unit through a wire line or a wireless communication line;
- selecting a choice from a plurality of choices;
- transmitting the choice in a control e-mail to the analysis unit;
- receiving the control e-mail via the wire line or the wireless communication line;
- extracting a specific data from the control e-mail; and
- resuming operation of the analysis unit based on the specific data extracted.

8. The method according to claim 7, wherein the analysis unit comprises a liquid chromatograph.

* * * * *